United States Patent [19]
Brehmeier-Flick et al.

[11] Patent Number: 6,083,174
[45] Date of Patent: Jul. 4, 2000

[54] IMPLANTABLE MEASURING UNIT FOR INTRACORPORAL MEASUREMENT OF PATIENT DATA

[75] Inventors: Bernd Brehmeier-Flick, Rinteln; Christian Beck, Hannover; Guido Eckert, Bonn, all of Germany

[73] Assignee: SICAN GmbH, Hannover, Germany

[21] Appl. No.: 09/155,875

[22] PCT Filed: Feb. 12, 1998

[86] PCT No.: PCT/DE98/00406

§ 371 Date: Dec. 7, 1998

§ 102(e) Date: Dec. 7, 1998

[87] PCT Pub. No.: WO98/35610

PCT Pub. Date: Aug. 20, 1998

[30] Foreign Application Priority Data

Feb. 13, 1997 [DE] Germany ............ 197 05 474

[51] Int. Cl.[7] ............................................. A61B 5/00
[52] U.S. Cl. ................................. 600/561; 600/486
[58] Field of Search ........................... 600/485, 486, 600/488, 561; 73/727

[56] References Cited

U.S. PATENT DOCUMENTS

| | | | |
|---|---|---|---|
| 4,499,394 | 2/1985 | Koal | 310/330 |
| 4,519,401 | 5/1985 | Ko et al. . | |
| 4,685,469 | 8/1987 | Keller | 128/675 |
| 4,722,348 | 2/1988 | Ligtenberg et al. . | |
| 4,738,267 | 4/1988 | Lazorthes et al. . | |
| 5,263,244 | 11/1993 | Centa et al. . | |
| 5,951,487 | 9/1999 | Brehmeier-Flick et al. | 600/561 |

FOREIGN PATENT DOCUMENTS

| | | |
|---|---|---|
| 0413588 | 2/1991 | European Pat. Off. . |
| 0566354 | 10/1993 | European Pat. Off. . |
| 4315987 | 11/1994 | Germany . |
| 4341903 | 6/1995 | Germany . |
| WO 9320531 | 10/1993 | WIPO . |

OTHER PUBLICATIONS

L. Talamonti, et al., "Contactless Inductive–Operation Microcircuits for Medical Applications," IEEE Engineering in Medicine & Biology Society, Proc. of 10th Annual Intern. Conference, New Orleans, Nov. 4–7, 1988, pp. 818–819.

Leung et al, IEEE Transactions on Biomedical Engineering, vol. BME. 33 No. 4, Apr. 1986, pp. 386–394.

*Primary Examiner*—Max Hindenburg
*Attorney, Agent, or Firm*—Birch, Stewart, Kolasch & Birch, LLP

[57] ABSTRACT

A measuring system for measurement of patient data inside a patient's body includes a flexible foil for implantation into the patient's body. At least one sensor is arranged on the flexible foil. A first telemetry unit is also arranged on the flexible foil. The telemetry unit is provided for receiving an inductive power transmission and for transmitting data. Strip conductors electrically connect the at least one sensor element to the telemetry unit. Preferably, the at least one sensor includes a pressure sensor for sensing the patient's brain or cranial pressure. The at least one sensor may optionally include a temperature sensor the patient's brain temperature. A second telemetry unit is located outside the patient's body for receiving the data from the first telemetry unit and for transmitting the inductive power transmission to the first telemetry unit.

15 Claims, 2 Drawing Sheets

IMPLANTABLE MEASURING UNIT FOR INTRACORPORAL MEASUREMENT OF PATIENT DATA

This application is the national phase under 35 U.S.C. §371 of prior PCT International Application No. PCT/DE98/00406 which has an International filing date of Feb. 12, 1998 which designated the United States of America, the entire contents of which are hereby incorporated by reference.

BACKGROUND OF THE INVENTION

1. Field of the Invention

The invention pertains to an implantable measuring unit for the intracorporal measurement of patient data, particularly of brain (cranial) pressure, for mobile application in everyday conditions, and is an addition to registration DE 196 38 813.9 entitled "Intracorporal Implantable Measuring System".

2. Description of the Relevent Art

In medical applications, measurement probes are introduced into the body, e.g. the head (intracranial), with the aid of a catheter and routed to areas where bio-signals are to be measured. For measurements in the skull, the probes must have a very small diameter—which is why microsensors are preferred—which then are mounted in and bonded with a carrier sleeve.

For example, for the diagnosis of hydrocephalus symptoms, the brain (cranial) pressure is measured intracranially in the hospital's intensive care unit with a probe. Afterwards the probe is pulled out and destroyed, or sterilized in the case of multiple-use probes, and reused on the next patient.

When hydrocephalus, for example, has been diagnosed, a so-called shunt system is routed through, which guides cranial fluid into the abdominal cavity when the cranial pressure rises above an established value in order to avoid excessive pressure in the brain.

Cranial pressure can be measured both in an epidural and a subdural manner. Epidural means that the cranial pressure between the dura mater of the brain and the top of the skull is indirectly determined by the pressure exercised onto the dura mater of the brain by the cranial fluid.

This measurement location provides the advantages that the dura mater of the brain is not penetrated, and therefore an infection of the dura mater is prevented; that the procedure is considerably easier; that no brain tissue is damaged during the measuring process; and that the sensor can remain in its measurement location for an extended period of time.

Subdural measurement means that the sensor is slid under the dura mater of the brain, which must be penetrated for this procedure. Furthermore, the pressure in the brain tissue (parenchyma) can now be measured as well, and often the brain tissue is penetrated in order to enable measurements in the ventricle (intraventricular).

There are various known intracranial measurement systems. For example, Braun Melsungen AG offers an epidural measurement system by the name of "Epidyn". Here a micro pressure sensor is fastened in a metal housing. The sensor is connected with the cords of a cable through which electric signals can be sent to an extracorporal evaluation unit.

Another epidural system is available from Spiegelberg, where a balloon catheter is slid under the top of the skull. Depending on the cranial pressure which the dura mater of the brain transfers to the balloon, the pressure is routed to the outside via a line and can be measured there extracorporally.

Camino offers an intraventricular cranial pressure measuring system with a beam waveguide where pressure measurements can be conducted according to the reflection measurement procedure via a silicone oxide level which changes its position, and therefore its reflection coefficient, depending on the pressure. The reflecting portion is put into a ratio to the light percentage that is sent; this provides information about the intraventricular pressure. The system offers the advantage during a TÜV (German Department of Transportation) approval that no electric streams or tensions occur intracorporally.

In addition, single-use intraventricular and parenchymal "low-cost" cranial pressure sensors are available. Since the spring of 1995, Codman (Johnson & Johnson) has been offering a brain pressure sensor with piezo-resistive technology which is adjusted through a switch with trimming potentiometer in the socket.

The measurement systems mentioned above require in-patient treatment of the patient to conduct the pressure measurements because the feeding tubes are very sensitive. It is desirable, however, to measure and record intracorporal pressures under normal living conditions of the patient at regular intervals.

Furthermore, the patient's freedom of movement is limited by being hooked up to the monitors via the catheter. This makes caring for the patient very labor-intensive even though he or she would otherwise be capable of taking care of himself or herself, both emotionally and physically. In addition, there is the risk of incorrect measurements and equipment failures during movement of the patient.

Particularly for the implantation of a shunt system for cranial fluid drainage, an implantable measurement system for controlling the catheter cross-section and the valve opening pressure would be very desirable.

U.S. Pat. No. 4,519,401 describes a telemetric, intracranial pressure measurement implant which requires no cable connections to recording and evaluation units located extracorporally. For this, the first radio unit transmits the measurement signals of a pressure and temperature sensor to a second radio unit. The first radio unit is implanted under the scalp and is connected with the intracorporal sensors. The patient carries the second radio unit with him extracorporally. Both radio units have a sender and a receiver. At established times, the sensors are activated with an impulse which is transmitted from the second radio unit to the first radio unit. The measurement data is then transmitted from the first to the second radio unit where it can be memorized and displayed on a monitor. The above-described system turns the sensors on and off at pre-adjusted intervals. In doing so, however, it is possible that a sudden pressure increase may not be recorded. Additionally, the record density of the measurement data remains constant, independent of the data relevance. It is not possible to obtain a continuous measuring signal because the data intervals of the measurement values are too low. By utilizing radio signals, relatively high transmission output in the vicinity of the brain is required, which could possibly have damaging side effects.

The German disclosure document DE 43 41 903 A1 describes an implantable telemetric endosystem whose outer dimensions are smaller than 1.0 mm×1.5 mm×0.6 mm. The implantable measuring system has a sensor in connection with a telemetry unit that is coupled inductively to an extracorporal receiving device. The implantable system is supplied inductively with power from the outside so that no batteries have to be implanted. Suggested data transmission procedures include amplitude, frequency and pulse-width modulation. A method for arranging, fastening and wiring the pressure sensor and the telemetry unit is not included in the description.

In "Contactless Inductive-Operation Microcircuits for Medical Applications", by L. Talamonti, G. Porroveccio, and G. Marotta, in IEEE Engineering in Medicine & Biology Society, Proc. of the 10th Annual Intern. Conference, New Orleans, Nov. 4–7, 1988, pages 818–819, an implantable telemetry unit that can be integrated on a chip with pressure and/or temperature sensors is presented. The telemetry unit, however, should be inserted directly beneath the skin for an operation that is free from disruptions and tolerable for the patient. This would make the layout of the pressure/temperature sensor and telemetry unit described not advantageous, however, because the sensor has to be inserted in defined areas of the body, such as in the cranial fluid or under the dura mater of the brain. In practice, this would mean a separation of the sensor from the telemetry unit.

Conventional systems utilize a cable connection between the sensor and the transmission unit, e.g. telemetry unit. The cable connections' realization is very labor and cost-intensive and prone to defects. Additionally, implantation requires great skill on the part of the physician because the cables cannot be slid under the skin and can break and become twisted during the implantation procedure.

SUMMARY OF THE INVENTION

Based on this level of technology, it was the object of the invention to create a measuring unit with an implantable part for mobile utilization to measure cranial pressure with a simple and inexpensive method of fastening and a connection between the sensor and the telemetry unit. The physician should be able to implant the measuring unit without difficulty or complications.

A sensor element and a telemetry unit are wired with strip conductors in an inexpensive and reliable manner. The sensor element and telemetry unit are arranged on a flexible foil which can be implanted easily because it can be slid under the skin without twisting or being moved in an undesirable direction. Therefore, the hole that must be made in the top of the skull can be done at a smaller diameter than has been practiced until now.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

A new type of cranial pressure measuring system is presented as the preferred implementation example. The measuring system can also be used for other medical applications.

Figure 1:
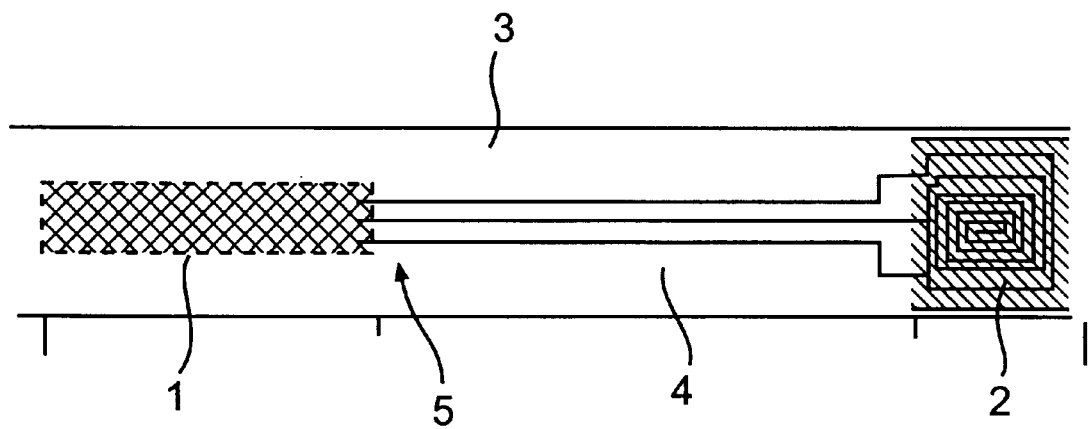
FIG. 1 is a top view of the implantable measuring system with a sensor element and a telemetry unit on a foil.

FIG. 1 shows a schematic view of the implantable part of the measuring system. A sensor element 1 is implanted with at least one sensor, e.g. for pressure. Additionally, depending on the requirements, other sensors, e.g. for temperature, can be provided for. The sensor element 1 is connected to a telemetry unit 2, i.e. with an inductive coupling element that is implanted as well. The telemetry unit 2 has an outer spool via which the implanted circuit is supplied inductively with power. In addition, data measured in the sensor element 1 is transmitted with inductive coupling to an evaluation unit. This ensures that the implantation of a battery is no longer required.

The sensor element 1 and the telemetry unit 2 are arranged on a flexible foil 3 which has strip conductors 4 for the purpose of connecting the sensor element 1 and the telemetry unit 2 electrically. This eliminates the conventional extensive wiring layout with twisted cables. In addition, the flexible foil 3 is very easy to implant because it can be slid under the skin without twisting or being moved in an undesirable direction. This way, the hole to be drilled into the top of the skull can be of a smaller diameter than before. Furthermore, only a very small cut of the skin is required because the foil 3, with the sensor element 1 and the telemetry unit 2 arranged on top, is very narrow.

Figure 2:
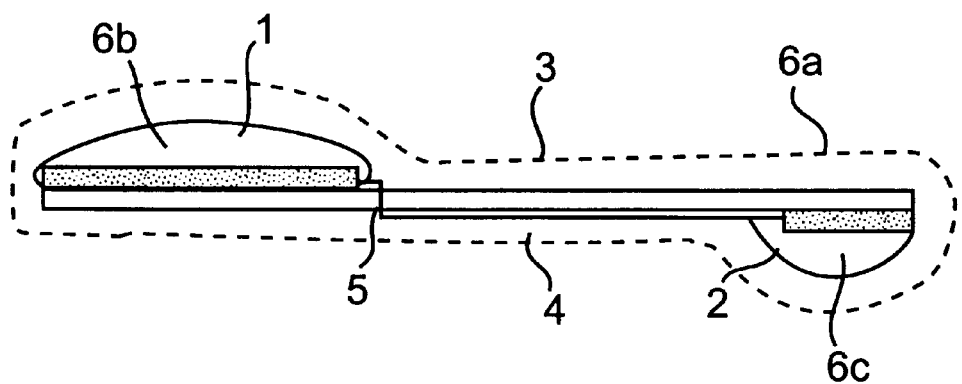
FIG. 2 is a cross-section of the implantable measuring system of FIG. 1.

FIG. 2 shows the implantable measuring unit's cross-section. It reveals that the sensor element 1 and the telemetry unit 2 are arranged in a particular way on opposite sides of the foil 3 respectively. Throughplating 5 for the strip conductor 4 is planned in order to guide it to the opposite side. The entire implant is coated with a silicone layer 6a for the protection of the patient. In addition, the sensor element 1 and the telemetry unit 2 are coated, respectively, for protection purposes with a layer 6b, 6c.

Figure 3:
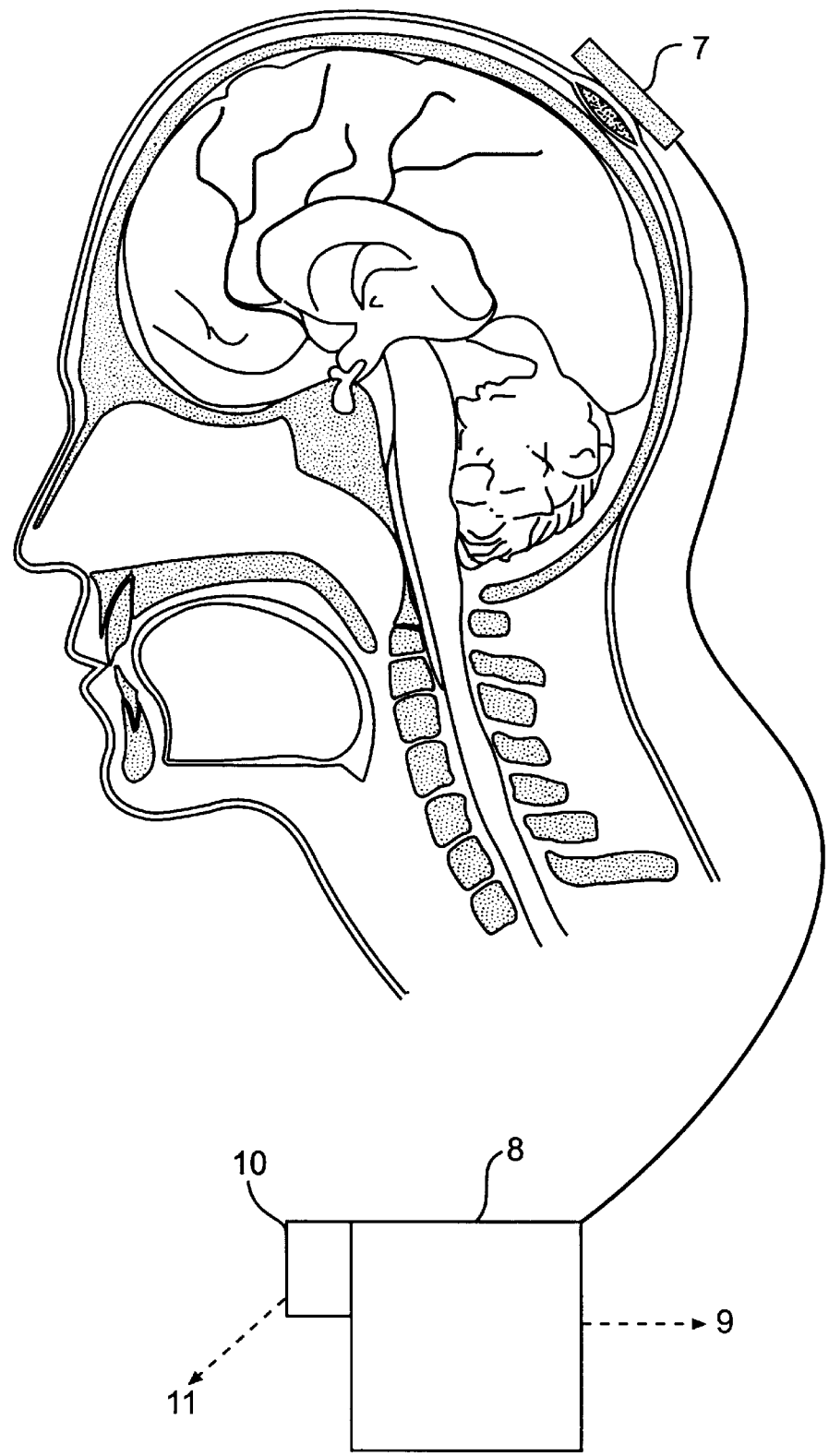
FIG. 3 illustrates a mobile measuring unit for extracorporal data transmission and evaluation.

FIG. 3 indicates that the data is routed from the implantable measuring unit to a recording unit 8 via an extracorporal telemetry unit 7 after measurements over an extended period of time. From there, the data can be transmitted e.g. via a serial interface to a personal computer 9, or the like, or via a data card 10, e.g. PCMCIA, to a portable computer or mobile telephone 11. The data is then evaluated in a powerful arithmetic unit and used as an aid for medical diagnoses.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A measuring system for measurement of patient data inside a patient's body, said system comprising:
   a flexible foil for implantation into the patient's body;
   at least one sensor arranged on said flexible foil;
   a first telemetry unit arranged on said flexible foil, said telemetry unit for receiving an inductive power transmission and for transmitting data; and
   strip conductors electrically connecting said at least one sensor element to said telemetry unit.

2. The system according to claim 1, wherein said at least one sensor includes a pressure sensor.

3. The system according to claim 2, wherein said pressure sensor is for sensing a brain pressure.

4. The system according to claim 2, wherein said at least one sensor includes a temperature sensor.

5. The system according to claim 4, wherein said temperature sensor is for sensing a brain temperature.

6. The system according to claim 1, further comprising:
a second telemetry unit for positioning outside the patient's body and for having communications with said first telemetry unit.

7. The system according to claim 6, wherein said communications include receiving said data from said first telemetry unit.

8. The system according to claim 6, wherein said communications include transmitting said inductive power transmission to said first telemetry unit.

9. The system according to claim 8, wherein said communications include receiving said data from said first telemetry unit.

10. The system according to claim 6, wherein said at least one sensor includes a pressure sensor.

11. The system according to claim 10, wherein said pressure sensor is for sensing a brain pressure.

12. The system according to claim 10, wherein said at least one sensor includes a temperature sensor.

13. The system according to claim 12, wherein said temperature sensor is for sensing a brain temperature.

14. The system according to claim 1, wherein said at least one sensor is located on one side of said flexible foil, and said first telemetry unit is located on an opposite side of said flexible foil.

15. The system according to claim 1, wherein said strip conductors are arranged on said flexible foil.

* * * * *